(12) United States Patent
Lemme et al.

(10) Patent No.: US 7,935,534 B2
(45) Date of Patent: May 3, 2011

(54) AUTOMATED MOLECULAR PATHOLOGY APPARATUS HAVING FIXED SLIDE PLATFORMS

(75) Inventors: Charles Lemme, Tucson, AZ (US); Devon Campbell, Tucson, AZ (US); Andrew Ghusson, Tucson, AZ (US); David Bryant, Tucson, AZ (US); Kurt Reinhardt, Tucson, AZ (US); William Richards, Tucson, AZ (US); Vincent Rizzo, Tucson, AZ (US); Wayne Showalter, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 12/818,369

(22) Filed: Jun. 18, 2010

(65) Prior Publication Data
US 2010/0255532 A1 Oct. 7, 2010

(51) Int. Cl.
*G01N 35/00* (2006.01)
(52) U.S. Cl. ............... 436/43; 436/45; 436/46; 436/50; 436/180; 422/63; 422/64; 422/65; 422/66; 422/67; 422/68.1

(58) Field of Classification Search ............ 436/43, 436/45–46, 50, 180; 422/63–68.1, 100, 105
See application file for complete search history.

(56) References Cited

U.S. PATENT DOCUMENTS

| | | | | |
|---|---|---|---|---|
| 5,075,079 | A * | 12/1991 | Kerr et al. .................. | 422/64 |
| 5,358,691 | A * | 10/1994 | Clark et al. ................. | 422/64 |
| 5,425,918 | A * | 6/1995 | Healey et al. ............... | 422/64 |
| 5,595,707 | A * | 1/1997 | Copeland et al. ............ | 422/64 |
| 6,093,574 | A * | 7/2000 | Druyor-Sanchez et al. .. | 436/180 |
| 6,352,861 | B1 * | 3/2002 | Copeland et al. ........... | 436/46 |
| 6,495,106 | B1 * | 12/2002 | Kalra et al. ................ | 422/100 |
| 6,582,962 | B1 * | 6/2003 | Richards et al. ............ | 436/46 |
| 6,783,733 | B2 * | 8/2004 | Bogen et al. ............... | 422/64 |
| 6,998,270 | B2 * | 2/2006 | Tseung et al. .............. | 436/46 |

* cited by examiner

*Primary Examiner* — Brian R Gordon
(74) *Attorney, Agent, or Firm* — Ventana Medical Systems, Inc.; Richard D. Schmidt

(57) ABSTRACT

Apparatus and methods for automatically staining or treating multiple tissue samples mounted on slides are provided, in which the slides and reagent bottles are held in fixed position, and the reagent, wash and coverslipping solutions brought to the slides. Alternatively, the slides are held in fixed position, while the reagent, wash and coverslipping solutions brought to the slides.

3 Claims, 19 Drawing Sheets

AUTOMATED MOLECULAR PATHOLOGY APPARATUS HAVING FIXED SLIDE PLATFORMS

CROSS REFERENCE TO RELATED APPLICATION

This Application claims benefit of priority from U.S. application Ser. No. 11/558,257, which is a continuation of U.S. application Ser. No. 10/424,372, filed Apr. 28, 2003, now U.S. Pat. No. 7,378,055, and U.S. Provisional Application Ser. No. 60/375,679 filed Apr. 26, 2002.

FIELD OF THE INVENTION

The present invention is directed to apparatus for use in diagnostic molecular pathology and, more particularly, to such apparatus used for the automated staining and/or treating of tissue samples mounted on microscope slides.

BACKGROUND OF THE INVENTION

Molecular pathology is the examination at a molecular level of the DNA, mRNA, and proteins that cause or are otherwise associated with disease. From this examination important information about patient diagnosis, prognosis, and treatment options can be elucidated. The practice of molecular pathology is generally divided into two main areas: (i) analysis of DNA, mRNA, and proteins in intact cells (in-situ), and (ii) analysis of these biological materials after they have been extracted from tissues. The first category, to which the present invention is primarily directed, has the advantage that it allows the pathologist or scientist to study the histopathologic architecture or morphology of the tissue specimen under the microscope at the same time that the nucleic acid or proteins are being assayed. These techniques include immunohistochemistry (IHC) which looks at proteins, in-situ hybridization (ISH) which looks at nucleic acids, histochemistry (HC) which looks at carbohydrates, and enzyme histochemistry (EHC) which looks at enzyme chemistry. For example, ISH can be used to look for the presence of a genetic abnormality or condition such as amplification of cancer causing genes specifically in cells that, when viewed under a microscope, morphologically appear to be malignant. ISH is also useful in the diagnosis of infectious diseases as it allows detection not only of a microbial sequence but also of precisely which cells are infected. This may have important clinicopathologic implications and is an effective means to rule out the possibility that positive hybridization signal may have come from an adjacent tissue of no clinical concern or from blood or outside contamination.

IHC utilizes antibodies which bind specifically with unique epitopes present only in certain types of diseased cellular tissue. IHC requires a series of treatment steps conducted on a tissue section or cells (e.g. blood or bone marrow) mounted on a glass slide to highlight by selective staining certain morphological indicators of disease states. Typical steps include pretreatment of the tissue section to remove the paraffin and reduce non-specific binding, retrieval of antigens or cell conditioning masked by cross-linking of the proteins from the chemical fixatives, antibody treatment and incubation, enzyme-labeled secondary antibody treatment and incubation, substrate reaction with the enzyme to produce a fluorophore or chromophore highlighting areas of the tissue section having epitopes binding with the antibody, counterstaining, and the like. Most of these steps are separated by multiple rinse steps to remove unreacted residual reagent from the prior step. Incubations can be conducted at elevated temperatures, usually around 37° C., and the tissue must be continuously protected from dehydration. ISH analysis, which relies upon the specific binding affinity of DNA or RNA probes with unique or repetitive nucleotide sequences from the cells of tissue samples or bodily fluids, requires a similar series of process steps with many different reagents and is further complicated by varying temperature requirements.

In view of the large number of repetitive treatment steps needed for both IHC and ISH, automated systems have been introduced to reduce human labor and the costs and error rate associated therewith, and to introduce uniformity. Examples of automated systems that have been successfully employed include the ES®, NexES®, DISCOVERY™, BENCHMARK™ and Gen II® staining Systems available from Ventana Medical Systems (Tucson, Ariz.). These systems employ a microprocessor-controlled system including a revolving carousel supporting radially positioned slides. A stepper motor rotates the slide carousel placing each slide under one of a series of reagent dispensers positioned above the slides. As described in U.S. Pat. No. 6,352,861 B1, bar codes on the slides and reagent dispensers fully automate the computer-controlled actuation of the dispensers onto the slides so that different reagent treatments can be performed for each of the various tissue samples.

Instrumentation such as the Ventana Medical Systems ES®, Gen II® NexES®, BENCHMARK® and DISCOVERY® systems are fundamentally designed to sequentially apply reagents to tissue sections mounted on one by three inch glass microscope slides under controlled environmental conditions. The instrument must perform several basic functions such as reagent application, washing (to remove a previously applied reagent), jet draining (a technique to reduce the residual buffer volume on a slide subsequent to washing), Liquid Coverslip™ application (a light oil application used to contain reagents and prevent evaporation), and other instrument functions.

The Ventana Medical Systems staining instruments mentioned above process slides on a rotating slide carousel. The instrumentation described herein has the slides fixed in a stationary position and rotates the basic processing stations above the fixed slides. The following details of how the slides are processed, the process algorithm, is the same regardless of the physical configuration.

The process of staining tissue on a slide consists of the sequential repetition of the basic instrument functions described above. Essentially a reagent is applied to the tissue then incubated for a specified time at a specific temperature. When the incubation time is completed the reagent is washed off the slide and the next reagent is applied, incubated, and washed off, etc, until all of the reagents have been applied and the staining process is complete.

It is desirable to permit any staining protocol for any of the slides being run, i.e. any combination of reagents and incubation times. In addition, to stain multiple slides as quickly as possible the instrument should process the slides simultaneously. This is feasible given that most of the time slides are just incubating, thus freeing up time to perform the washing, reagent application and other functions on other slides.

One algorithm to accomplish simultaneous staining (sometimes referred to as the "random access" method) is to create a task and time schedule for each slide in the run, then perform each task on each slide when the schedule calls for it. The problem with this method is that incubation times will not be accurate if the instrument is busy performing a task on one slide when it is time to be washing another slide (thereby completing incubation on that slide). The variation in incubation times will be unpredictable since the total number of slides and the slide protocols vary.

Slide processing using a lock-step algorithm insures that all incubation times are accurate and predictable irrespective of the number of slides processed or the variation in slide protocols. While incubation times are assured, the lock step algorithm implies that incubation times must be an increment of the fundamental incubation time period. For example, with an incubation cycle of two minutes, the total incubation times must be multiples of two, i.e., two, four, six, eight etc. minutes in duration. However, the preferred embodiment of the present invention uses a four minute incubation time. Generally this is not a particular limitation since typical incubation times are an order of magnitude longer than the fundamental incubation period.

Prior art staining systems typically include either convection or radiation to warm the samples above laboratory ambient temperatures for steps requiring elevated temperatures. Heating the slide improves staining quality by acceleration of the chemical reaction and can permit a reaction temperature more closely matching body temperature (about 37° C.) at which antibodies are designed to react. While such convection or radiant heating systems have been generally suitable for IHC, which is antibody-based, they are less suitable for ISH, which is nucleic acid-based and requires higher and more precise temperature control in order to denature DNA. In order to denature the DNA double helix of both the target sample and the probe so as to render them single stranded, the temperature must be raised above the melting point of the duplex, usually about 94° C. Precise temperature control is also required in ISH to effect probe hybridization at the desired stringency. The selected temperature must be low enough to enable hybridization between probe and target, but high enough to prevent mismatched hybrids from forming.

Hot air convection, conduction or radiant heat heating units typically employed with prior art automated tissue stainers do not permit the temperature of individual slides to be separately controlled. With prior art systems all of the slides are heated to the same temperature at any given time during the process. For example, U.S. Pat. Nos. 5,645,114 and 6,180,061 to Bogen et al. disclose a dispensing assembly adapted to carry a plurality of microscope slides. Individual slide holders containing resistive heating units are provided. However, with the assembly taught by Bogen et al., all of the slides would be heated to a common temperature because no means are disclosed for separate heating controls or for shielding slides from heat generated by adjacent slides.

Other difficulties frequently encountered in both IHC and ISH testing results from the manner in which the tissues are typically preserved. The mainstay of the diagnostic pathology laboratory has been for many decades the formalin-fixed, paraffin-embedded block of tissue, sectioned and mounted upon glass slides. Fixation in such a preservative causes cross-linking of macromolecules, both amino acids and nucleic acids. These cross-linked components must be removed in the case of ISH, to allow access of the probe to the target nucleic acid, and, in the case of IHC, to allow the antibody to recognize the corresponding antigen. "Unmasking" the antigen and/or nucleic acid is typically accomplished manually with multiple pretreatment, protolytic digestion, and wash steps.

Prior to staining, complete removal of the paraffin is also required so that it does not interfere with antibody or probe binding. Manual deparaffinization normally is achieved by the use of two or three successive clearing reagents that are paraffin solvents such as xylene, xylene substitutes or toluene. However, new automated methods that are largely based on physical separation mechanisms are revealed in U.S. Pat. No. 6,544,798 B1 to Christensen et al., which do not require toxic solvents and are aqueous-based.

The foregoing discussion of the prior art largely derives from Richards et al. U.S. Pat. No. 6,296,809, assigned to Ventana Medical Systems, in which there is described apparatus and methods for automatically staining or treating multiple tissue samples mounted on microscope slides so that each sample can receive an individualized staining or treatment protocol even when such protocols require different temperature parameters. More specifically, there is described in the '809 patent apparatus comprising a computer controlled, bar code driven, staining instrument that automatically applies chemical and biological reagents to tissue or cells mounted or affixed to standard glass microscope slides. According to the '809 patent, a plurality of slides are mounted in a circular array on a carousel which rotates, as directed by the computer, to a dispensing location placing each slide under one of a series of reagent dispensers on a second rotating carousel positioned above the slides. Each slide receives the selected reagents (e.g. DNA probe) and is washed, mixed and/or heated in an optimum sequence and for the required period of time.

According to the '809 patent, individual slides are carried on thermal platforms radially mounted to the carousel. Temperature sensors are also mounted to the slide carousel, individually monitoring and controlling each thermal platform separately. Apparatus made in accordance with the '809 patent is available commercially from Ventana Medical Systems, of Tucson, Ariz. as the DISCOVERY® or BENCHMARK® systems.

The present invention is a modification and improvement over the prior art including the apparatus and methods described in the '809 patent. More particularly, the present invention rather than bringing the slides to the reagent, stain, and wash stations, brings the reagent, stain and wash stations to fixedly positioned slides. That is to say, in the present invention the slides are fixedly positioned in the apparatus, and the various washing, staining and reagent fluids are selectively delivered to the slides. Fixing the slides in position in the apparatus simplifies wiring to the heaters, and also eliminates the potential that a slide may be dislocated by rapid start and stop movement of the slide carousel, which, in a worst case scenario could result in a domino or train-wreck effect where one dislocated slide hits the neighboring slide causing that slide to dislocate, and so forth.

BRIEF DESCRIPTION OF THE DRAWINGS

Further features and advantages of the present invention will be seen from the following detailed description, taken in conjunction with the accompanying drawings, wherein like numerals depict like parts, and wherein.

DETAILED DESCRIPTION OF THE INVENTION

Figures 1, 1A:
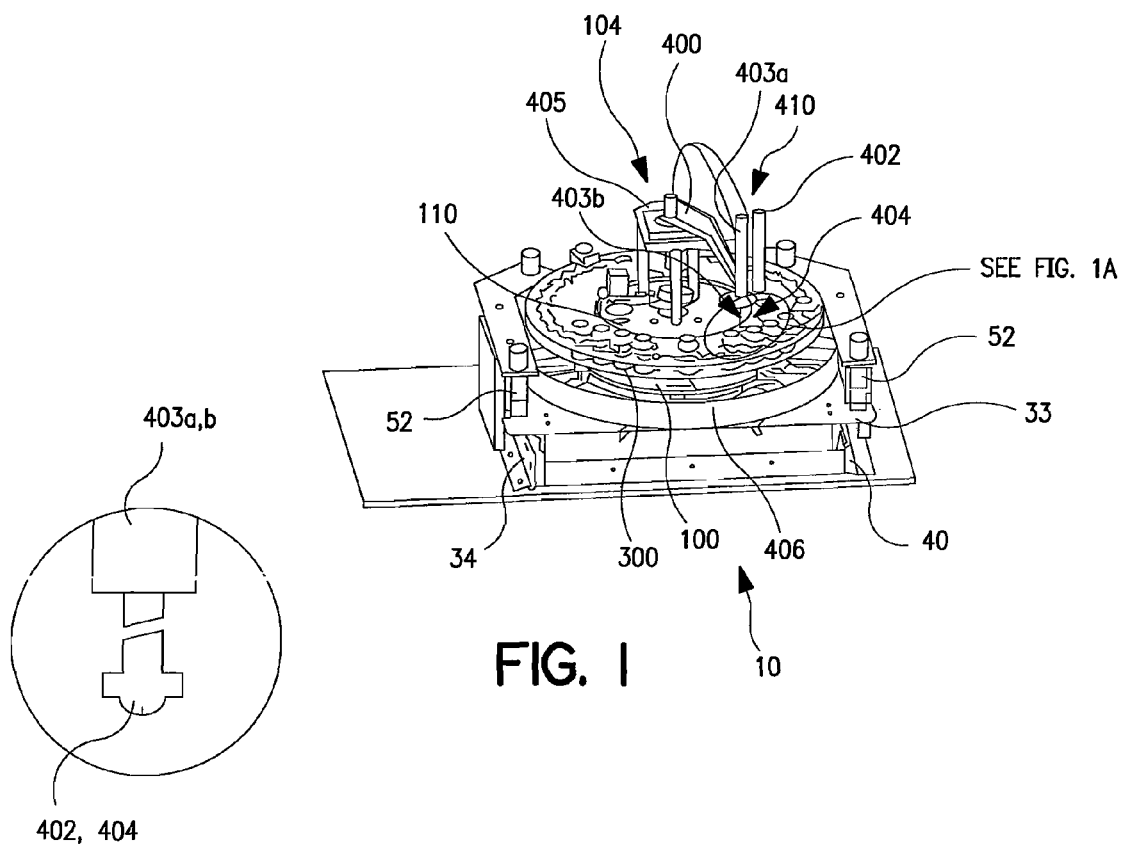
FIG. 1 is a perspective view of a first embodiment of an apparatus of the present invention shown with the slide cabinet shell removed.
FIG. 1A is an enlarged view showing details of portions of the reagent transfer probes.

Referring now in detail to the drawings wherein like parts are designated by like reference numerals throughout, there is illustrated in FIG. 1 a perspective view of the molecular pathology apparatus according to a first embodiment of the present invention which is designated generally by reference numeral 10. For the purposes of clarity, several of the reagent bottles, as well as the cabinet shell, and liquid and air supply tubing and electrical wiring are omitted from the drawings. Apparatus 10 is designed to automatically stain or otherwise treat tissue mounted on microscope slides with nucleic acid probes, antibodies, and/or other reagents in a desired sequence, time and temperature. Tissue sections so stained or treated are then to be viewed under a microscope by a medical practitioner who reads the slide for purposes of patient diagnosis, prognosis, or treatment selection.

Figure 2:
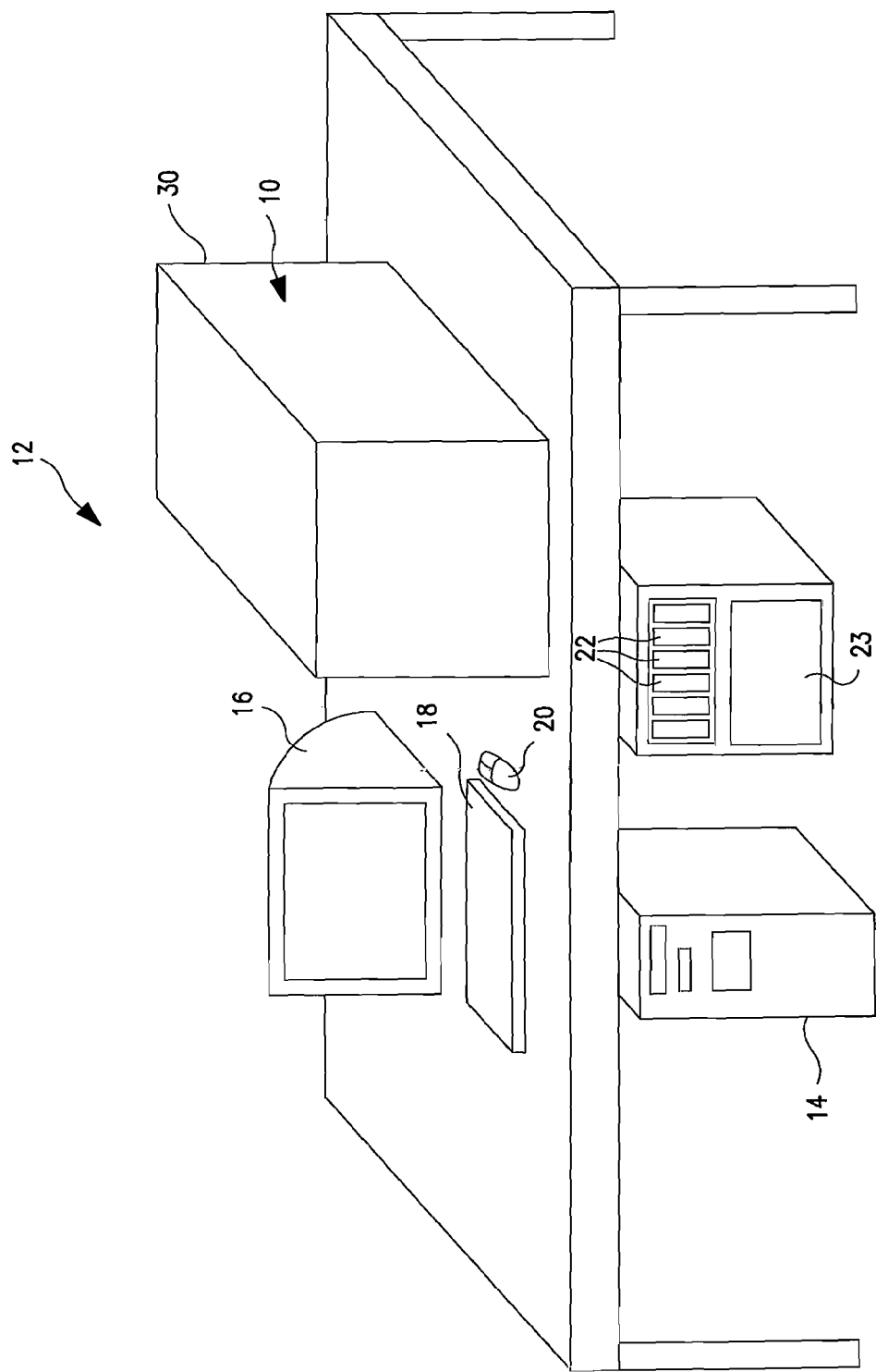
FIG. 2 is a perspective view of the apparatus of FIG. 1, first embodiment shown in conjunction with a computer and other instruments with which it operates.

In the first embodiment, apparatus 10 functions as one component or module of a system 12 (FIG. 2) which also comprises a host computer 14 preferably a personal computer, monitor 16, keyboard 18, mouse 20, bulk fluid containers 22, waste container 23 and related equipment. Additional staining modules or other instruments may be added to system 12 to form a network with computer 14 functioning as a server. Alternatively, some or all of these separate components could be incorporated into apparatus 10 making it a stand-alone instrument.

Referring also to FIGS. 3, 3A and 4-7, as set forth in greater detail below, a plurality of slide platforms 50 (FIGS. 4, 5) are mounted radially about a center point 32 of drawer 34 (FIG. 1) upon which standard glass slides 60 with tissue samples may be placed. Drawer 34 is slidably mounted in housing 30 on rails 40 or the like. The temperature of each slide may be individually controlled by means of sensors and a microprocessor, i.e. as taught in the above-mentioned '809 patent.

Each of the slide platforms 50 is connected through individual wires to a multiplexer (not shown) which is then in turn connected to a microprocessor (not shown). A feature and advantage of the present invention which results from fixedly mounting the slide platforms in drawer 34 is that each of the heaters and thermal sensors may be hardwired thereby eliminating the need for a slip ring assembly or rotor couplings, as well as complex stepping motors, etc. for locating and positioning a rotating slide carousel as required in prior art devices. Also, the possibility that a slide or slides may be shifted or dislocated during rapid start and stop rotation of the slide carousel is eliminated.

In one embodiment, a plurality of slots or channels are formed on the top surface of each of the slide heaters, i.e. the interface surface between the slide heater and the slide, for gathering and venting gas bubbles as may form during heating, i.e. in accordance with co-pending U.S. application Ser. No. 09/953,417, filed Sep. 11, 2001, and assigned to the common assignee, which disclosure is incorporated herein by reference.

Referring also to FIGS. 1, 2, 5 and 6, drawer 34 supports a slide support tray 33 which in turn supports a circular pan 35 having a peripheral wall 36 serving as a splash guard, a peripheral trough 37 and a central drain 38, i.e. at center point 32, both connected to drain lines 39 which in turn are connected to waste container 23. Drawer 34 is slidably mounted in housing 30 on rails 40. Rails 40, in a preferred embodiment, comprise three piece telescoping rails so that the drawer 34 may be slid clear of housing 30 to permit access to all of the slide platforms 50 for slide loading and removal. A damping means such as a pneumatic means, electromotive means, mechanical spring damper or the like preferably is provided to smooth movement of the drawer whereby to avoid possible dislodging of slides, particularly when the drawer is closed. Slide support tray 33 is supported on a lift mechanism such as pneumatic cylinders 52 (see FIG. 1), which automatically index to permit the slide support tray 33 to move up and down so that the slide support tray 33 and circular pan 35 may be dropped to permit wall 36 to clear the nozzle support 100 when the drawer is slid in and out of the apparatus.

Slide drawer 34 is divided into thirty-five equal pie-shaped sections 70. Thirty of the pie-shaped sections 70 are occupied by slide platforms 50 while the five remaining pie-shaped sections 70A (FIG. 4) at the rear of the drawer are devoid of slide platforms 50. In other words, a row of thirty slide platforms 50 are radially mounted on drawer 34 and evenly spaced from one another, except at the ends of the row.

However, the invention is not limited to thirty active slide locations, and more or fewer slide locations may be employed. An alternative embodiment may be implemented by aligning the platforms 50 linearly, which results in potentially limitless number of platforms.

Figure 3:
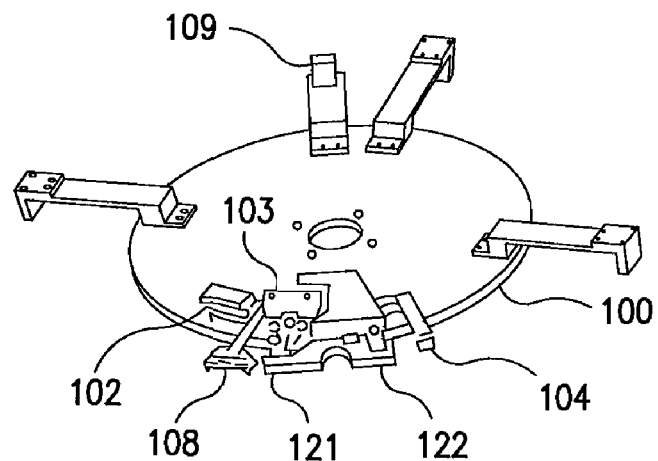
FIG. 3 is a perspective view and FIG. 3A is a partially exploded view of details of the nozzle support portion of FIG. 1, first embodiment.
Figure 3A:
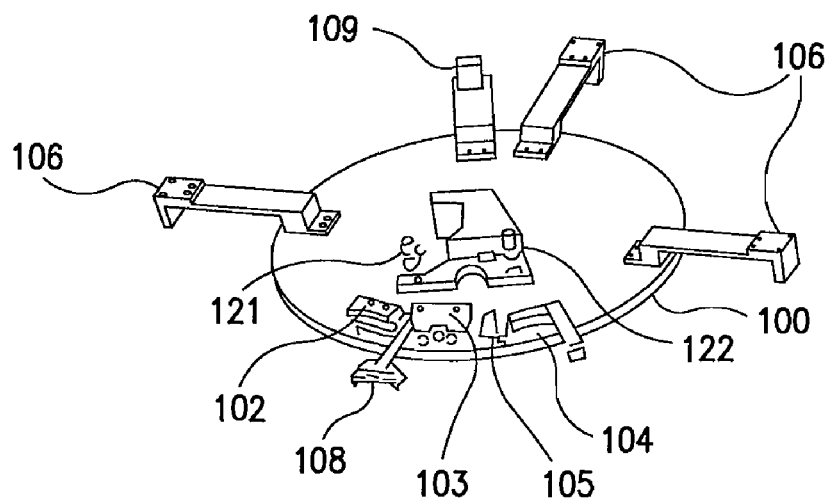
Figure 4:
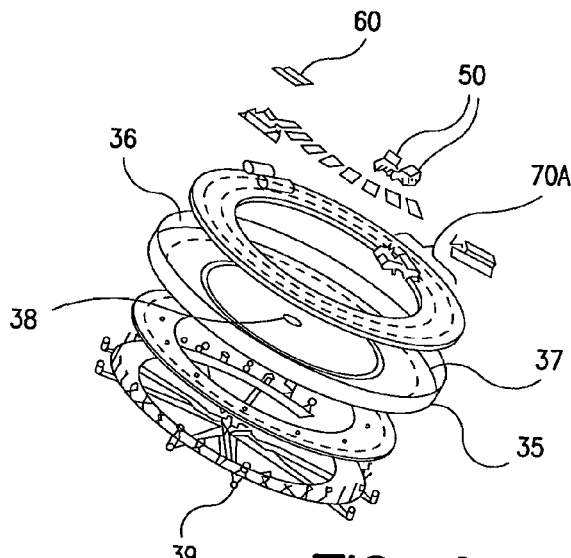
FIG. 4 is an exploded view of details of the slide plate portion of FIG. 1, first embodiment.
Figure 5:
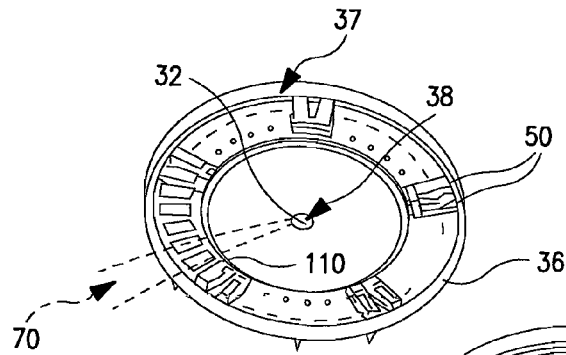
FIGS. 5 and 6 are perspective views, from the top and the bottom, respectively, of portions of the slide plate portion of FIG. 1, first embodiment.
Figure 6:
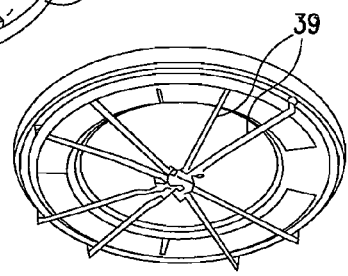

Referring to FIGS. 1 and 3, a nozzle support 100 is concentrically and rotatably mounted above slide drawer 34. Nozzle support 100 is mounted on a shaft (not shown) supported by a bridge 110, and driven by a computer controlled stepping motor and drive belt (not shown), and rotates plus or minus approximately 180° from a home position 104 at the rear of the drawer. The computer controlled stepper motor and drive belt are conventional in this art. Accordingly, details are omitted for the sake of clarity.

Nozzle support 100 carries the various slide treatment stations, other than the reagent dispensing location. Thus, nozzle support 100 carries dual rinse nozzle block 102, volume adjust/stringency block 103, Liquid Coverslip™ evaporation inhibitor liquid application block 105, vortex mixer air jet block 106, jet drain 108, and the like, all for preparing a slide for staining, stain removal, and the like, and to clear bar codes (not shown) carried on the slides, and a bar code reader 109, all as described in detail in U.S. Pat. Nos. 5,595,707; 5,650, 327; 5,654,199; or 5,654,200 to Copeland et al, which disclosures are incorporated herein by reference. In other words, nozzle support 100 carries all of the functions for slide preparation, cleaning, reagent mixing, Liquid Coverslip™ application, etc. other than reagent application, as described, e.g. in the '707 patent to Copeland et al., plus wash stations 121, 122 for the reagent application probes as will be described in detail below.

Preferably, but not necessarily, the various rinse nozzle blocks, vortex mixer air jet blocks, jet drain, etc. are arranged adjacent to one another so that the nozzle support 100 may be indexed and advanced in a "lock-step" manner to sequentially treat a slide according to an accepted protocol. For example, jet drain 108 may be arranged immediately adjacent rinse nozzle blocks 102 so that nozzle support 100 may be advanced in "lock step" manner past a selected slide, and the slide rinsed and fluid stripped, etc. Also, if desired, vortex mixer air jet blocks 106 may be oriented to impinge simultaneously on two adjacent slides.

For the sake of clarity, fluid and air supply tubing for the several slide treatment stations have been omitted from the drawings. It will be understood, however, that the fluid and air supply tubing are made long enough to permit the valve plate to rotate plus or minus. approximately 190° from a home position at the rear of the apparatus so that each slide treatment station can reach each slide 60. A pair of wash stations 121, 122 spaced two thirty-fifths of a revolution (approximately 20°) apart as will be described in detail hereinafter, are also attached to and radially extend beyond the periphery of the nozzle support 100, and rotate with the nozzle support 100.

Reagent support 300 is fixedly mounted to bridge 110 vertically above nozzle support 100, which arch in turn is fixedly mounted within housing 30. A plurality of reagent bottles 302 are removably mounted within recesses 304 formed equally spaced adjacent the periphery of reagent support 300. In the illustrated embodiment, a total of thirty-five reagent bottles are mounted on the reagent support 300, spaced approximately one thirty-fifth (approximately 10°) apart.

The reagents may include any chemical or biological material conventionally applied to slides including nucleic acid probes or primers, polymerase, primary and secondary antibodies, digestion enzymes, pre-fixatives, post-fixatives, readout chemistry, counterstains, and the like.

Figure 8:
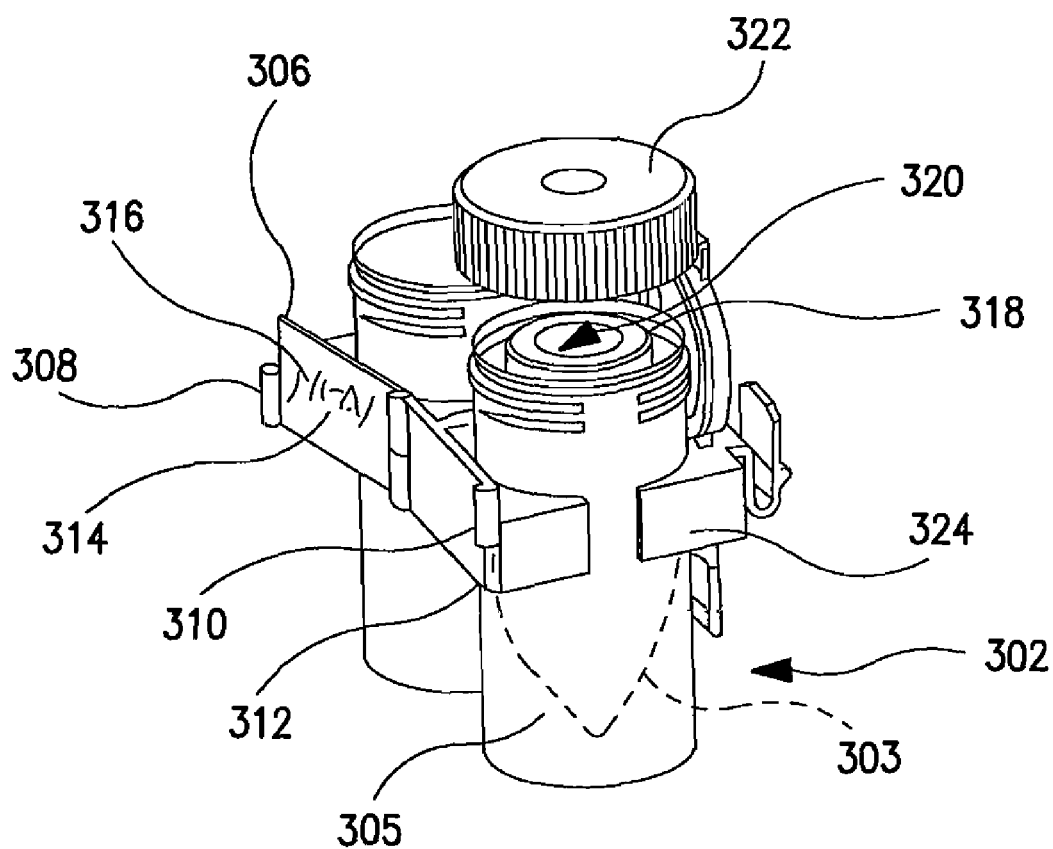
FIG. 8 is a partially exploded perspective view showing two reagent bottles of FIG. 1, first embodiment.
Figure 8A:
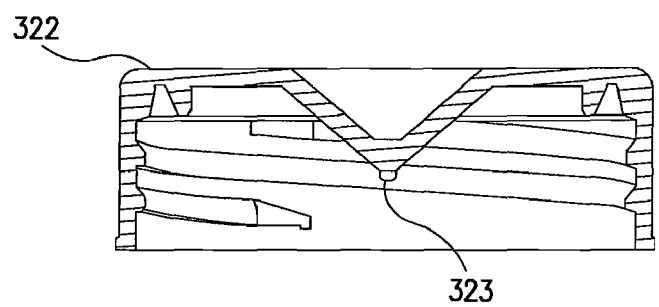
FIG. 8A is a cross-sectional view of a reagent bottle, cap and insert, first embodiment.
Figure 8A:
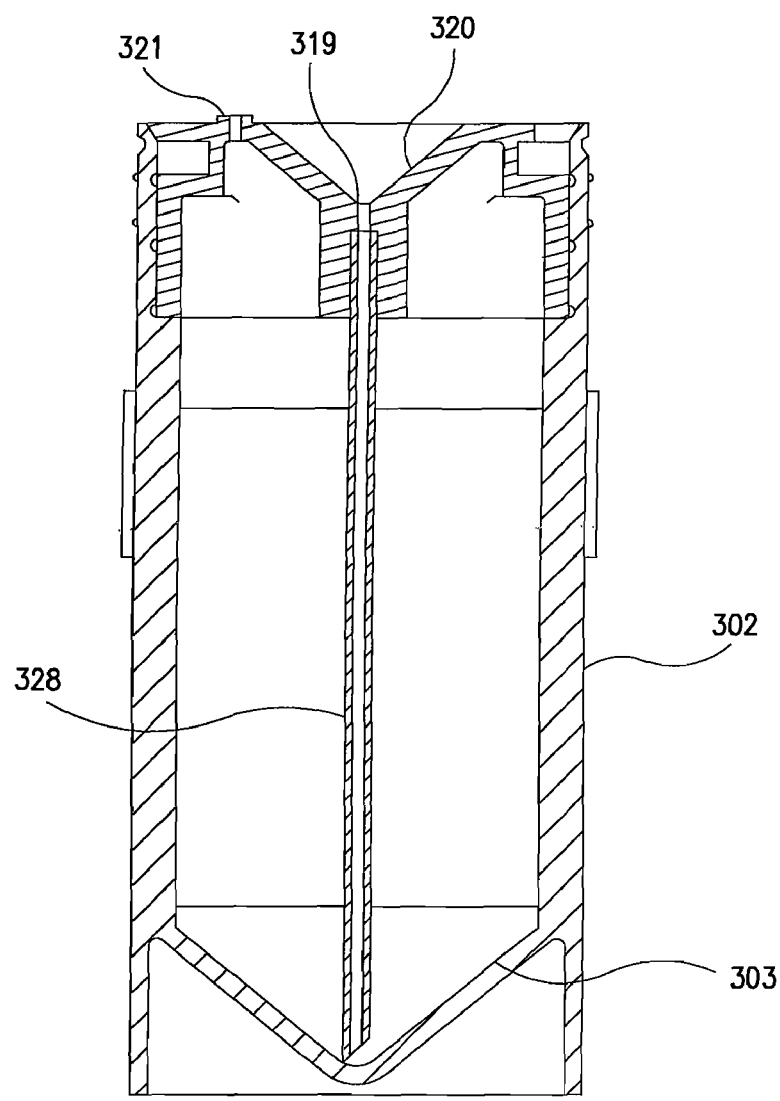

Referring also to FIG. 8, the reagent bottles 302 each comprise a cylindrical hollow body 305 closed at the bottom end by an integrally formed bottom wall. Preferably, the inside bottom wall of each bottle is cone shaped, i.e. as shown in phantom at 303 to facilitate reagent pick-up by reagent transfer probes as will be described in detail below. Each bottle 302 includes an integrally formed bracket 306 which serves to maintain the bottles 304 at a desired height in reagent support 300, and which may serve also to permit the stringing together of a plurality of like bottles 302. Accordingly, each bracket 306 includes a hinge element 308 for cooperating with a hinge element 310 of an adjacent bottle 302. In the illustrated embodiment, hinge elements 308 and 310 are shown as conventional pin-hinges in which the upper hinge 310 includes a pin 312 which fits into the lower hinge 308, i.e. similar to a conventional door hinge. However, bottles 302 may be hinged together in a variety of ways.

Bracket 306 preferably includes a flat surface 314 upon which is carried a bar code 316 for identifying the contents of the bottle 302. Bottles 302 also include an insert 318 having a tapered top surface 320 and inlet 319 fitted in the top end of the bottles for locating a reagent transfer probe 328 as will be described in detail hereinafter, and a cap 322 which may be either twist or snap-fitted to the bottle 302 for sealing the bottle 302.

Probe 328 is tapered at a lower end to fit closely in tapered conical bottom 303 of bottle 302. A vent 321 is formed in insert 318 for equalizing air pressure as reagent is removed. Cap 322 includes a tapered inner surface and plug 323 for sealing inlet 319.

Making brackets 306 attachable to one another permits one to assemble a chain of reagents for use, and also to remove the chain of reagents so that the reagents may be refrigerated, for example, overnight when not in use.

Figure 7:
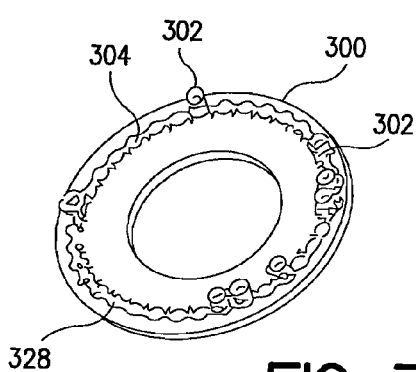
FIG. 7 is a perspective view of the reagent support portion of FIG. 1, first embodiment.
Figure 9:
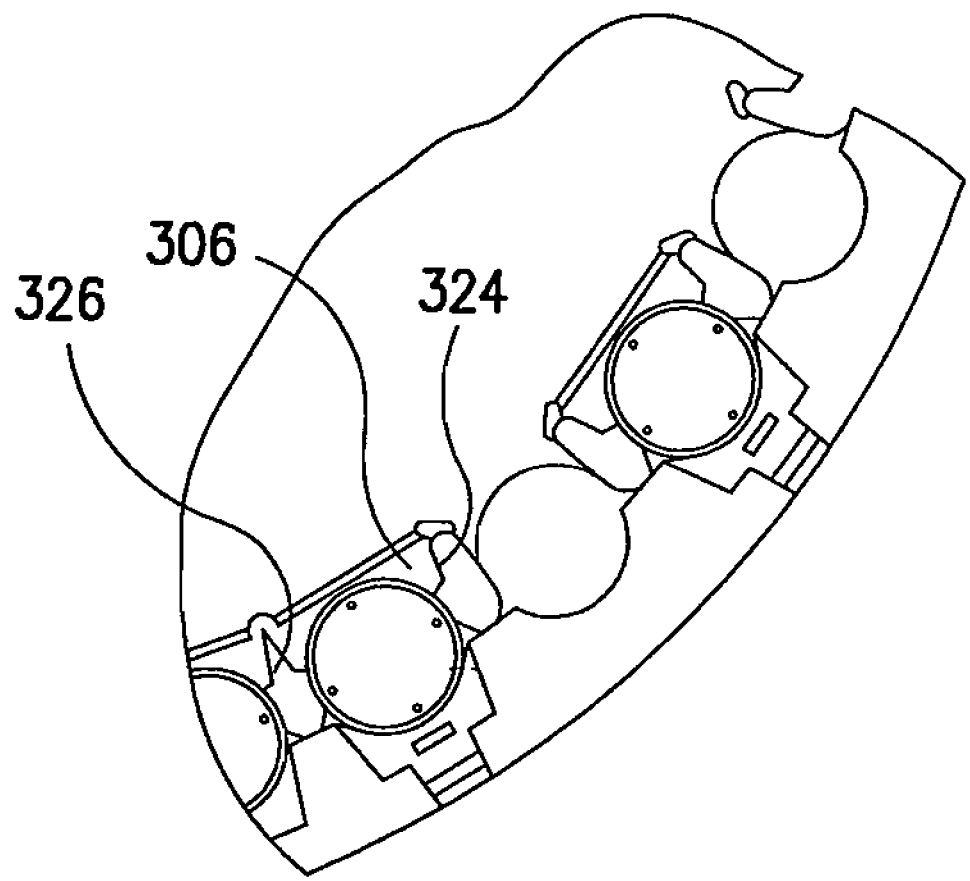
FIG. 9 is a top plan view of two reagent bottles of FIG. 1, first embodiment.

Referring next to FIGS. 7, 8 and 9, the side walls 324 of brackets 306 are tapered so that a pie-shaped space 326 is formed between two bottles when two bottles are fastened together in a string, and mounted in recesses 304 in the reagent support 300, thereby exposing holes 328 formed through reagent support 300. Holes 328 are formed in the same concentric circle as recesses 304, and are spaced equidistant between adjacent recesses 304. The purpose of pie-shaped spaces 326 and holes 328 is to provide clearance for reagent transfer probes 402, 404 as will be described in detail below.

Referring again to FIG. 1, an arm 400 is rotatably mounted on arch 405 concentrically above reagent support 300, and carries a pair of reagent transfer probes 402, 404 located at the distal end of arm 400 and spaced approximately 10° apart. Arm 400 also carries a bar code reader 406 for reading bar codes 316 on the reagent bottles. Arm 400 is rotatably driven by a computer driven stepping motor (not shown), and rotates plus or minus approximately 185° in either direction from a home position 410.

Reagent transfer probes 402 and 404, which are identical to one another, preferably comprise automatic pipette metering/dispensing pick-up devices designed to aspirate or "sip" reagent from a reagent bottle, move to a slide, and then "spit" or deposit the reagent onto the slide. "Sip" and "spit" automatic pipette/metering dispensing pick-up devices are described in published PCT Application No. PCT/US99/04379, which disclosure is incorporated herein by reference. Reagent transfer probes 402 and 404 are carried on the distal end of arm 400 and are spaced from one another so that when one of the probes, e.g. probe 402 is located centrally over a slide 60, the other reagent transfer probe 404 may be centrally positioned over one of the two probe wash stations 121 or 122. Pneumatic cylinders 403a, 403b selectively raise and lower probes 402 and 404 into one of the following positions: a raised transport position above the tops of the bottles 302 where the arm 400 is free to rotate; a reagent drawing position wherein one of the probes is inserted into a selected reagent bottle 302 wherein a measured amount of reagent may be drawn into the probe; a reagent dispensing position wherein a reagent transfer probe containing reagent is disposed in the pie-shaped space 326 between two reagent bottles, above a selected slide to dispense reagent thereon; and a cleaning position wherein the other probe, i.e. the probe not being used to dispense reagent, is operatively disposed in one of probe washing stations 121 or 122 which straddle the slide being dispensed upon. While the apparatus of the present invention could be made with only a single reagent transfer probe, providing two spaced reagent transfer probes improves cycle speed since reagent metering may be accomplished using one of the two reagent transfer probes while the other of the two reagent transfer probes is going through the wash cycle as will be described below. That is to say, while one of the reagent transfer probes, e.g. reagent transfer probe 402 is dispensing reagent onto a slide, the other reagent transfer probe, i.e. idle reagent transfer probe 404 may be lowered to a probe wash station 121 where the idle reagent transfer probe may be rinsed inside and out at the same time.

Figure 10A:
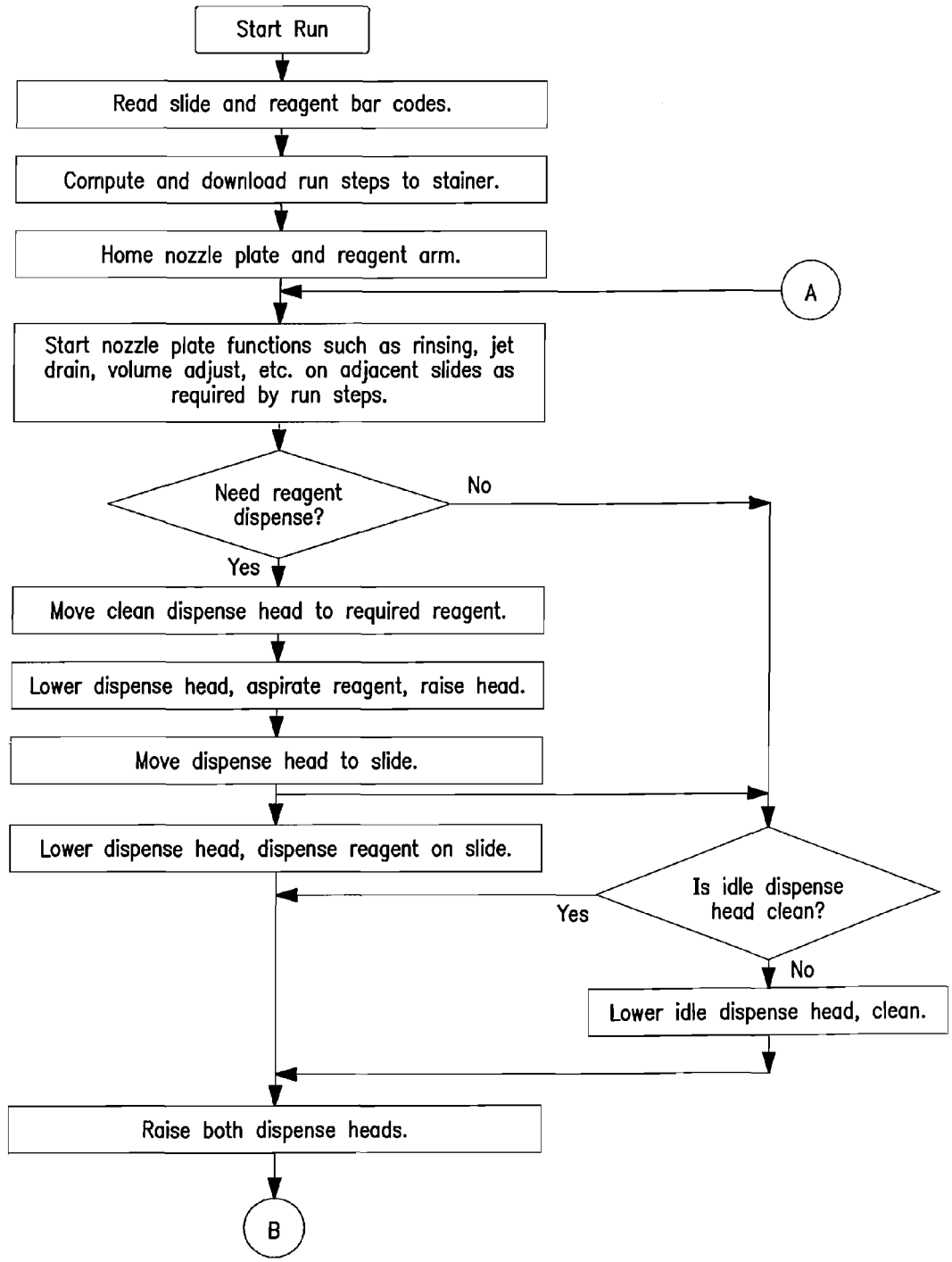
FIGS. 10A-10B are flow charts of the operation and control of FIG. 1, first embodiment.
Figure 10B:
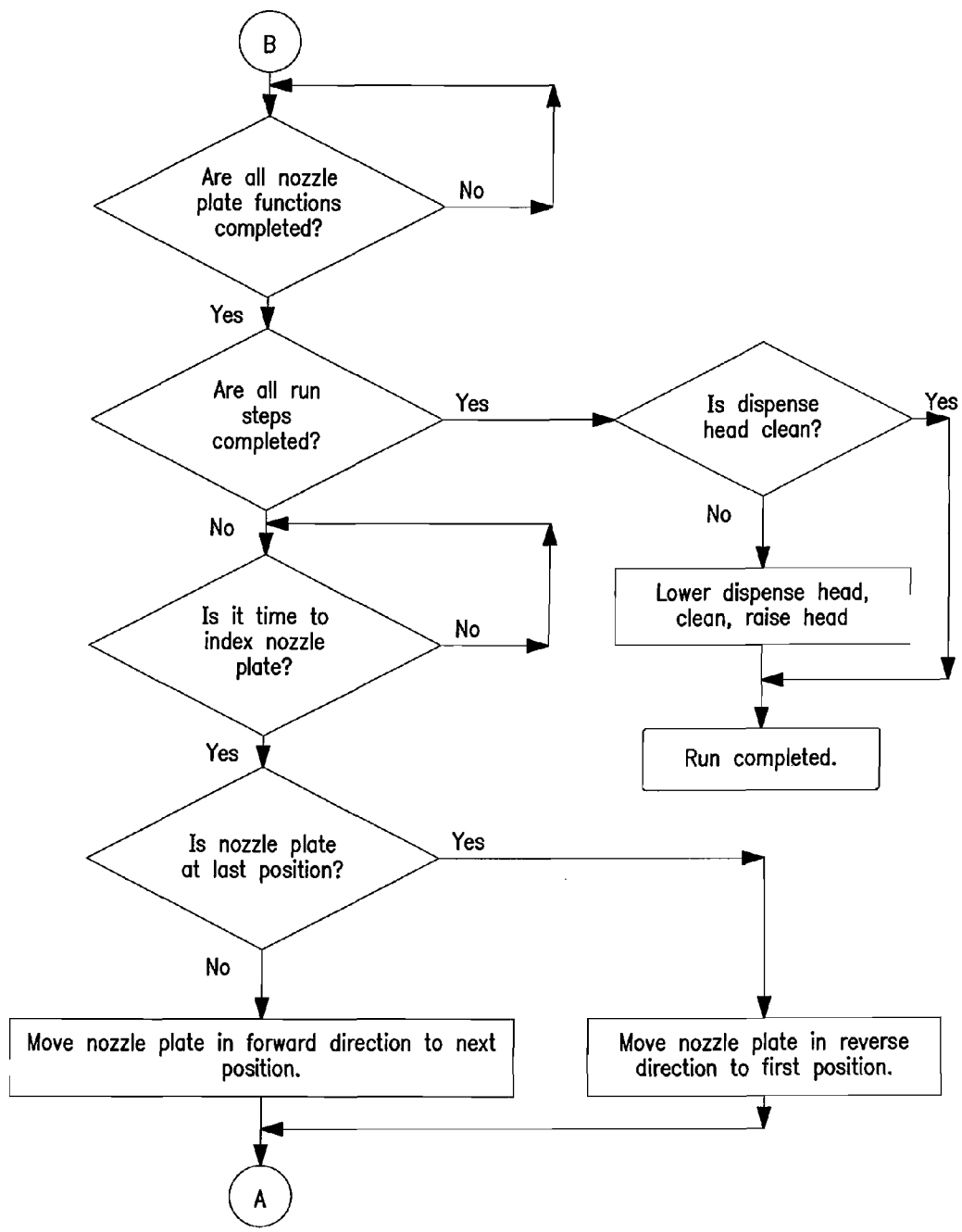

Referring to FIGS. 10A and 10B, the overall process is as follows:

A plurality of specimen-bearing slides 60 are mounted on the slide platforms 50, selected reagent bottles 302 mounted in the reagent support 300, the slide drawer is closed and the slide and reagent bar codes are read. The computer calculates the master protocol and then downloads the run steps for the entire run, the nozzle support 100 is indexed to the first slide, and the slide is washed and prepared for staining or other treatment in accordance with the pre-programmed run steps by advancing the nozzle support 100 in "lock-step" manner. In the meanwhile, probe arm 400 is rotated to the appropriate reagent bottle 302, one of the two reagent transfer probes 402 or 404 is indexed over the selected reagent bottle, and the probe lowered to aspirate a measured amount of the desired reagent. The reagent-containing transfer probe is then raised, and the arm 400 moved to the selected slide where the loaded reagent transfer probe is lowered to just over the slide, and the reagent dispensed on the slide. In the meanwhile, the idle reagent transfer probe is lowered into one of the washing stations 121 or 122, wherein the reagent transfer probe is washed inside and out. Both reagent transfer probes 402 and 404 are then raised, and the process repeated, but using the reagent transfer probe just cleaned in the previous step to aspirate and dispense reagent onto the next slide. As before, simultaneously with dispensing the reagent onto the slide as in the previous case, the idle reagent transfer probe is washed while the active reagent transfer probe is dispensing reagent onto the new slide.

The foregoing steps are repeated until all of the slides are processed. For convenience, in the illustrated embodiment, the dwell time at each slide station is six and two-thirds seconds. This comes from dividing a four minute cycle time into thirty-six time spaces, one time space for each of the thirty slide positions plus five blank slide positions for over-travel of the slide support, plus one "virtual" slide position for returning the nozzle support 100 from the last slide position to the first slide position. The virtual slide position allows the nozzle support 100 to return to the other end of its travel range in an uninterrupted fashion.

The staining algorithm used on the aforesaid Ventana systems avoids scheduling problems associated with random access methods by using a "lock step" method. The lock step algorithm requires that the nozzle support 100 which holds the processing functions be rotated one slide position index every "n" seconds, termed the slide index time. The slide index time is preferably as short as possible but long enough that the function that requires the longest time can be completed within the index time. In the embodiments of the inventions herein, "n" is six and two-thirds seconds. Index times are usually on the order of several seconds. The time for one complete rotation of the nozzle support 100, termed the fundamental incubation period, will then be "n" times the number of slide positions, including blank and virtual slide positions. (For example, if the slide index time is six seconds and there are twenty slide positions, the incubation time period will be 120 seconds or two minutes.)

Throughout the entire run the nozzle support 100 is indexed one slide position every "n" seconds. After the index, the system checks the schedule to see if any of the slides at each of the processing stations require the function of that station. For example, if the slide at the washing station is scheduled for washing, that slide is washed. Similarly if the slide at the reagent application station is scheduled for the application of a new reagent, then the new reagent is applied.

The above-described invention has several advantages over the prior art. For one, making the slide plate fixed in position eliminates the possibility of a slide being dislocated (and the sample dislodged) during the rapid start-stop rotational movement of a conventional rotating slide carousel. Also, employing two transfer syringes insures better cleaning of transfer syringes without increasing cycle time.

Also, since none of the moving elements, i.e. nozzle support 100 and probe support arm 400 need travel more than approximately 190° in either direction, all electrical connections, and air and fluid connections can be achieved without the need for slip ring or rotary connections, since the hoses and wires are quite capable of taking twistings of 190° plus.

The instrumentation described herein may or may not have the ability to continuously rotate the nozzle support. The nozzle support 100 may need to return to a starting position before rotation has exceeded 360 degrees. This may also be required when the slides are rotated on a carousel and the processing functions are fixed above the slides. Similarly, other non-rotating designs are possible such as linear or two dimensional configurations. In these cases there will be a requirement to move the slides or processing functions back to the original starting position during the staining run. In most cases it is likely that the time required to do this will exceed the index time which violates the fundamental requirement of the lock step algorithm. The lock step algorithm can still be utilized through the concept of the "virtual slide" previously mentioned. The virtual slide is added to the total number of actual slide positions so that the index time period assigned to the virtual slide may be used to move the slides or processing stations back to the starting position. Thus accurate and predictable incubation times are maintained.

While one embodiment of the invention has been described, the invention is susceptible to modification. For example, instead of using one or a pair of transfer syringes on an overhead arm, the reagent carousel could carry a plurality of micro-delivery reagent fluid dispensers such as described in U.S. Pat. Nos. 6,045,759; 6,416,713; or 6,192,945. Moreover, while the use of individually heated thermal platforms is preferred, the slides may be heated using conventional heating techniques.

Figure 11:
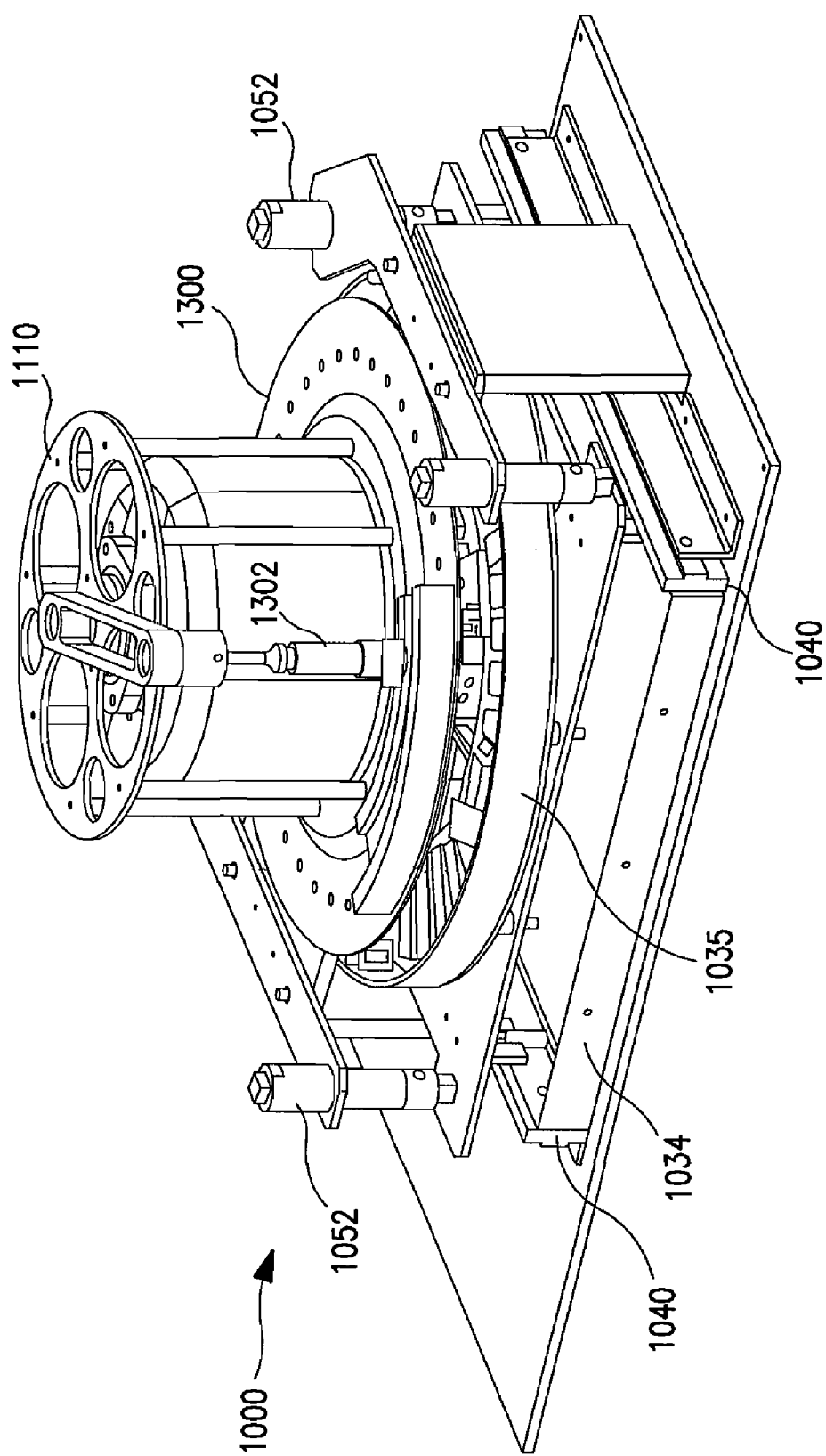
FIG. 11 is a perspective view of an alternative embodiment and apparatus of the present invention shown with the slide cabinet shell removed.
Figure 12:
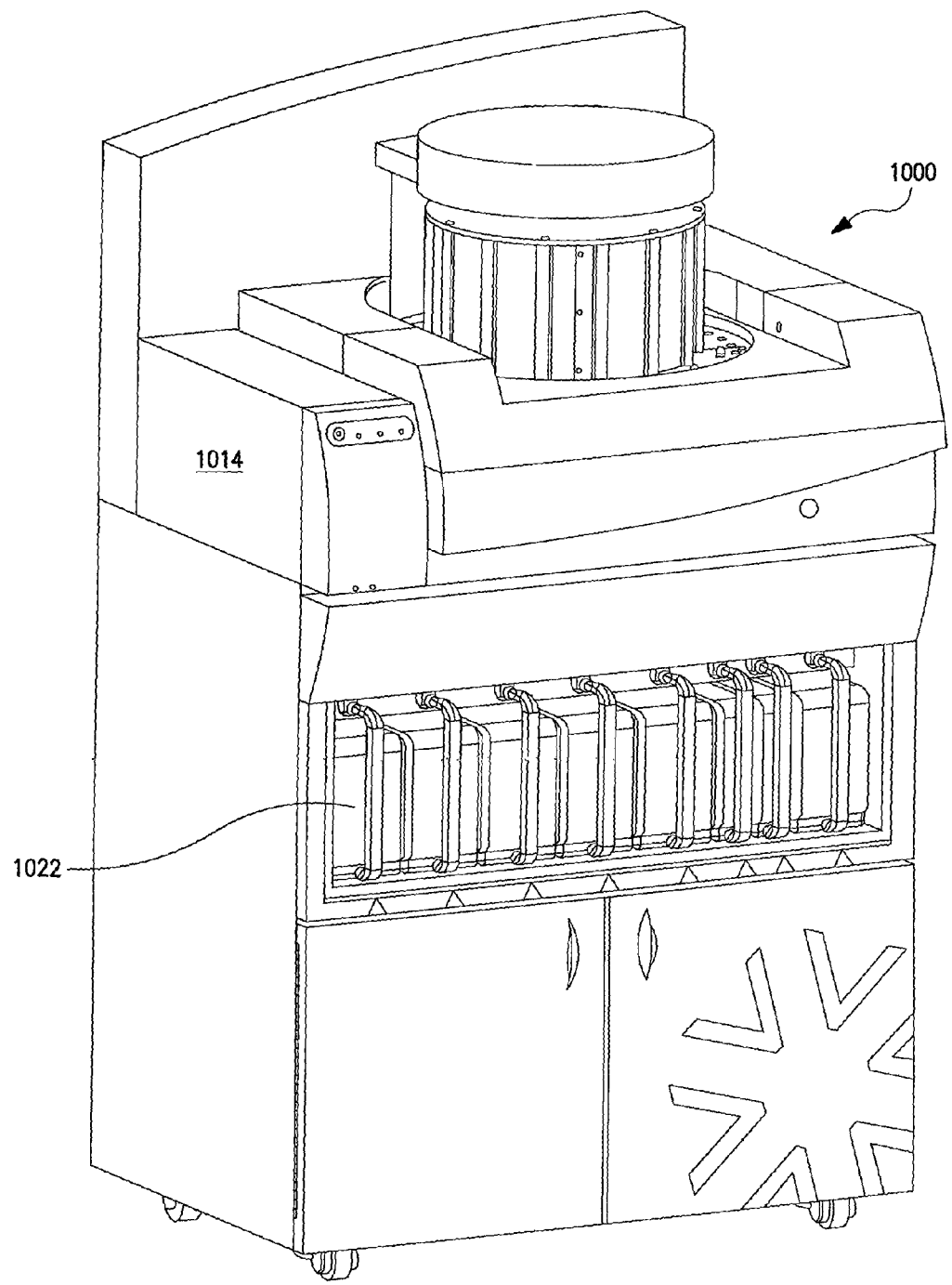
FIG. 12 is a perspective view of the FIG. 11 alternative embodiment shown in conjunction with a computer and other instruments with which it operates.

Referring to FIGS. 11-19, there is illustrated a second embodiment of the present invention. FIG. 11 is a perspective view of a molecular pathology apparatus according to the second embodiment which is designated generally by reference numeral 1000. For the purposes of clarity, all but one of the reagent dispensers and dispenser carriers, as well as the cabinet shell, and liquid and air supply tubing and electrical wiring are omitted from the drawings. Apparatus 1000 is designed to automatically stain or otherwise treat tissue mounted on microscope slides with nucleic acid probes, antibodies, and/or other reagents in a desired sequence, time and temperature. Tissue sections so stained or treated are then to be viewed under a microscope by a medical practitioner who reads the slide for purposes of patient diagnosis, prognosis, or treatment selection.

In one embodiment, apparatus 1000 (FIG. 12) functions as one component or module of a system which also comprises a host computer 1014 preferably a personal computer, bulk fluid containers 1022, waste container (not shown) and related equipment. Additional staining modules or other instruments may be added to the system to form a network with computer 1014 functioning as a server. Alternatively, some or all of these separate components could be incorporated into apparatus 1000 making it a stand-alone instrument.

Figure 14:
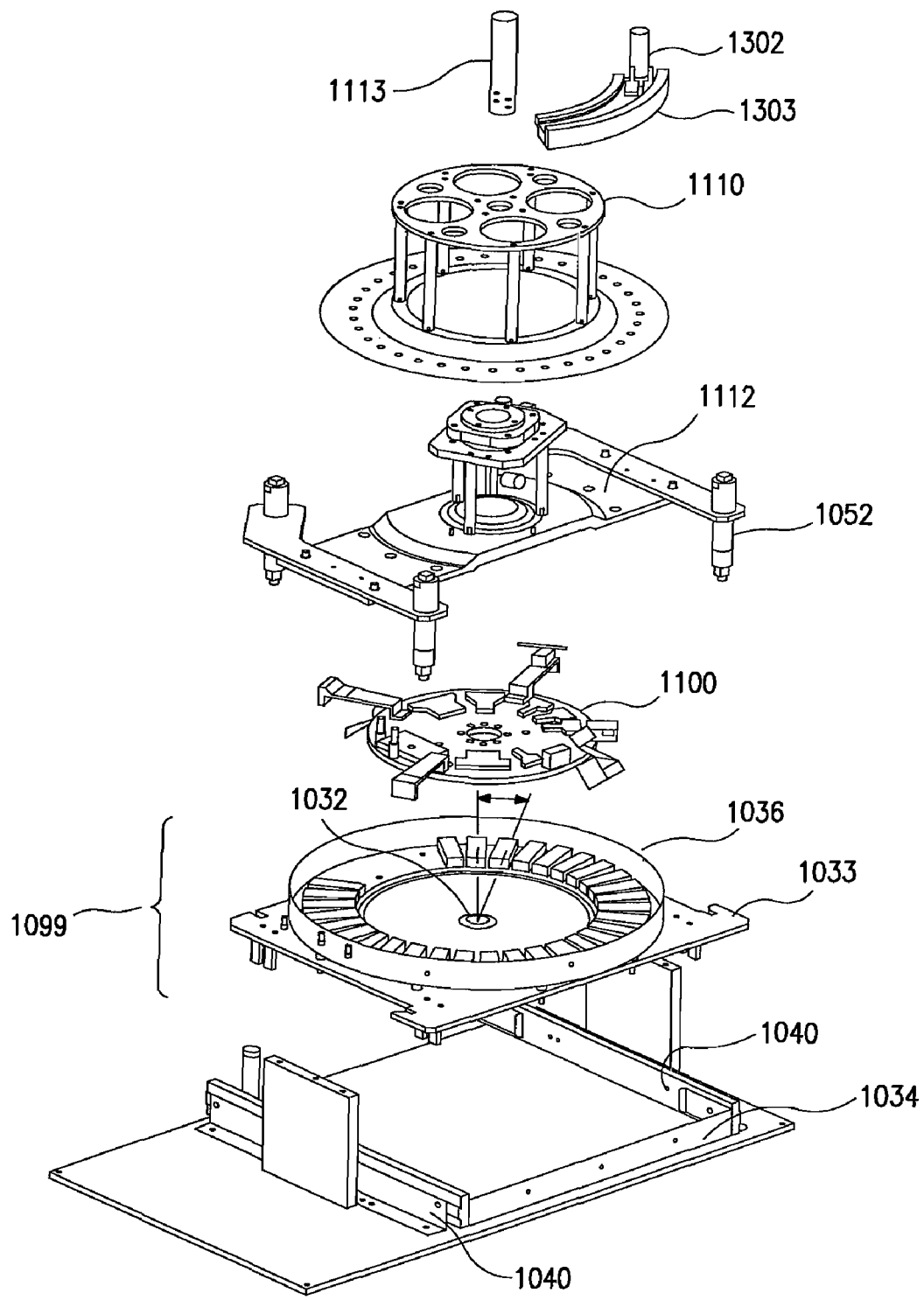
FIG. 14 is an exploded view of details of the FIG. 11 alternative embodiment.
Figure 15:
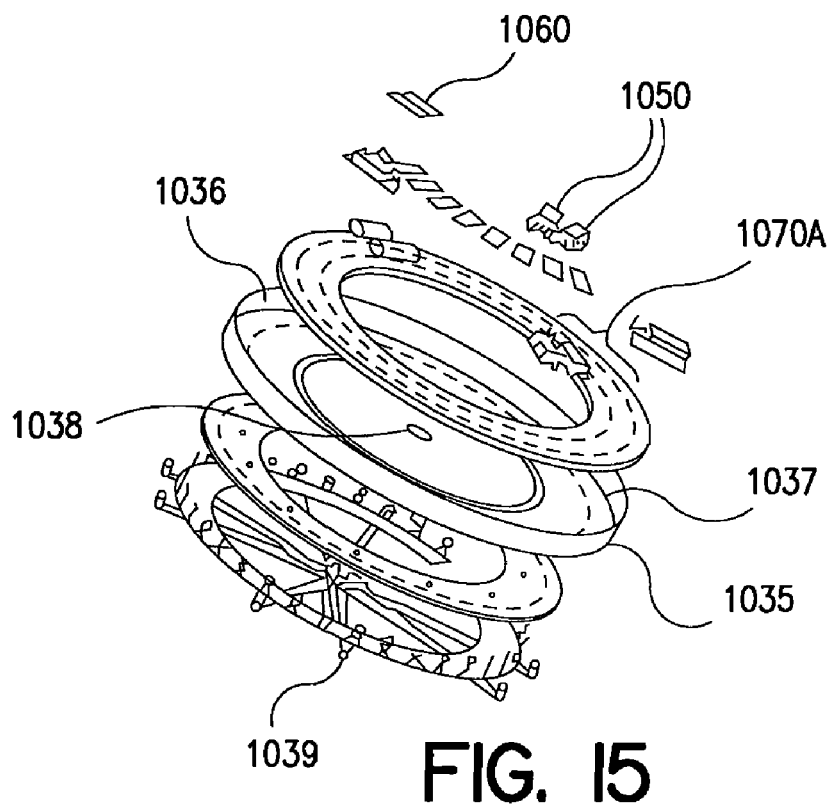
FIGS. 15 and 16 are perspective views, from the top and the bottom, respectively, of portions of the slide plate portion of the FIG. 11 alternative embodiment.
Figure 18:
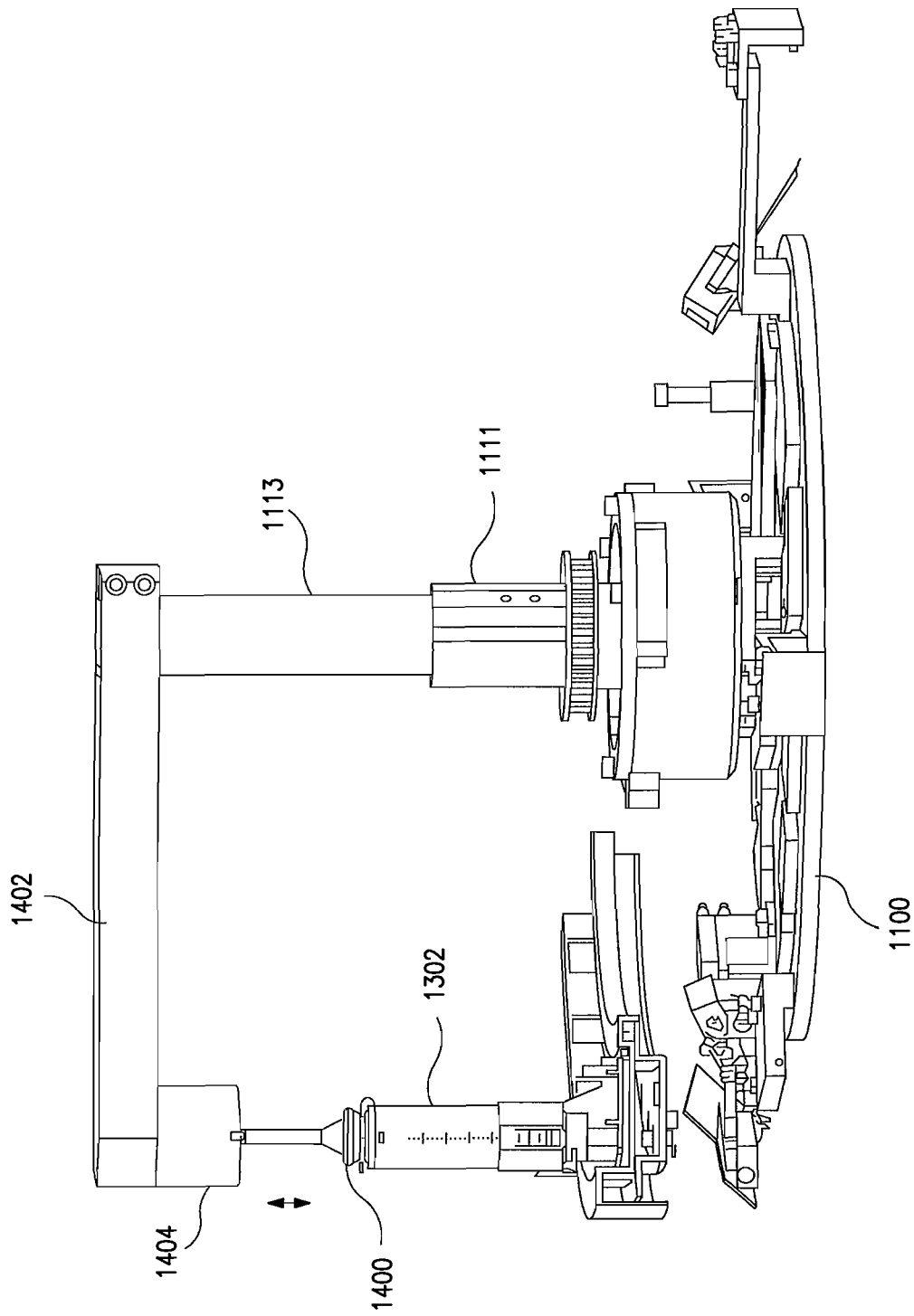
FIG. 18 is a perspective view showing details of the reagent dispenser activator portion of the FIG. 11 alternative embodiment.

Referring also to FIGS. 14, 15 and 18, as set forth in greater detail below, a plurality of slide platforms 1050 are mounted radially about a center point 1032 of slide support assembly 1099 upon which standard microscope glass slides 1060 with tissue samples may be placed. Drawer 1034 is slidably mounted in housing 1030 on rails 1040 or the like. The temperature of each slide may be individually controlled by means of temperature sensors and a microprocessor, i.e. as taught in the above-mentioned '809 patent.

As in the case of the first embodiment, each of the slide platforms 1050 is connected through individual wires to a multiplexer (not shown) which is then in turn connected to a microprocessor (not shown). Also, as in the case of the first embodiment, a plurality of slots or channels are formed on the top surface of each of the slide heaters, i.e. the interface surface between the slide heater and the slide, for gathering and venting gas bubbles as may form during heating, i.e. in accordance with co-pending U.S. application Ser. No. 09/953,417, filed Sep. 11, 2001, and assigned to the common assignee, which disclosure is incorporated herein by reference.

Figure 16:
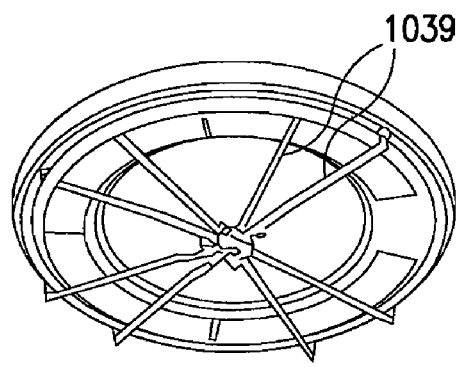

Referring to FIGS. 14-16, drawer 1034 supports a slide support assembly 1099 which is comprised of a slide support 1033 which in turn supports a circular pan 1035 having a peripheral wall 1036 serving as a splash guard, a peripheral trough 1037 and a central drain 1038, i.e. at center point 1032, both connected to drain lines 1039 which in turn are connected to waste container 1023. Drawer 1034 is slidably mounted in housing 1030 on rails 1040. Rails 1040, in a preferred embodiment, comprise three-piece telescoping rails so that the drawer 1034 may be slid clear of housing 1030 to permit access to all of the slide platforms 1050 for slide loading and removal. A damping means such as a pneumatic means, electromotive means, mechanical spring damper or the like (not shown) preferably is provided to smooth movement of the drawer whereby to avoid possible dislodging of slides, particularly when the drawer is closed. Slide support assembly 1099 is supported on a lift mechanism such as pneumatic cylinders 1052 (see FIG. 11), which automatically index to permit the slide support assembly 1099 to move up and down so that the slide support plate 1033 and circular pan 1035 may be dropped to permit wall 1036 to clear the nozzle support 1100 when the drawer is slid in and out of the apparatus.

Slide support assembly 1099 is allocated into thirty-five equal pie-shaped sections 1070. Thirty of the pie-shaped sections 1070 are occupied by slide platforms 1050 while the five remaining pie-shaped sections 1070A (FIG. 15) at the rear of the drawer are devoid of slide platforms 1050. In other words, a row of thirty slide platforms 1050 are radially mounted within slide support assembly 1099 and evenly spaced from one another, except at the ends of the row.

However, the invention is not limited to thirty active slide locations, and more or fewer slide locations may be employed. An alternative embodiment may be implemented by aligning the platforms 1050 linearly, which results in potentially limitless number of platforms.

Referring to FIGS. 11, 14 and 18, a nozzle support 1100 is concentrically and rotatably mounted above slide support assembly 1099. Nozzle support 1100 is mounted on a shaft 1113 which in turn is rotatably mounted on a bridge 1112, and driven by a computer controlled stepping motor and drive belt (not shown), and rotates plus or minus approximately 190° from a home position at the rear of the drawer. The computer controlled stepper motor and drive belt are conventional in this art. Accordingly, details are omitted for the sake of clarity.

Figure 13:
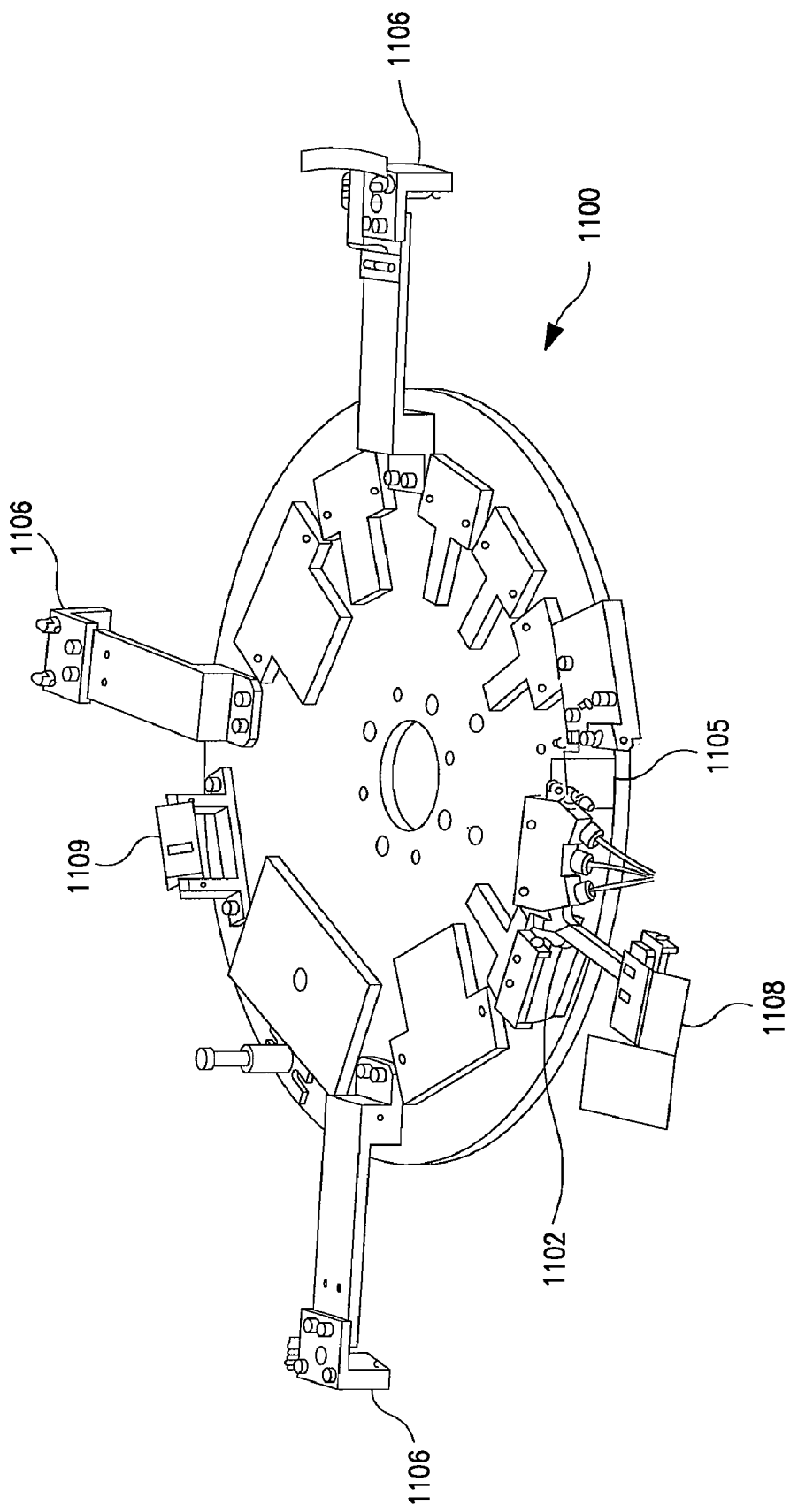
FIG. 13 is a perspective view showing details of the nozzle support portion of the FIG. 11 alternative embodiment.

With respect to FIG. 13, nozzle support 1100 carries the various slide treatment stations, other than the reagent dispensing station. Thus, nozzle support 1100 carries dual rinse nozzle block 1102, volume adjust/stringency block 1103, Liquid Coverslip™ evaporation inhibitor liquid application block 1105, vortex mixer air jet block 1106, jet drain 1108, and the like, all for preparing a slide for staining, stain reagent removal, and the like, and to clear the bar codes (not shown) carried on the slides, and a bar code reader 1109, all as described in detail in U.S. Pat. No. 5,595,707 to Copeland et al, which disclosure is incorporated herein by reference. In other words, nozzle support 1100 carries all of the functions for slide preparation, cleaning, reagent mixing, Liquid Coverslip™ application, etc. other than reagent application, as described in the '707 patent to Copeland et al.

Preferably, but not necessarily, the various rinse nozzle blocks, vortex mixer air jet blocks, jet drain, etc. are arranged adjacent to one another so that the nozzle support 1100 may be indexed and advanced in a "lock-step" manner to sequentially treat a selected slide according to an accepted protocol. For example, jet drain 1108 may be arranged immediately adjacent rinse nozzle blocks 1106 so that nozzle support 1100 may be advanced in "lock step" manner past a selected slide, and the slide rinsed and fluid stripped, etc. Also, if desired, vortex mixer air jet blocks 1106 may be oriented to impinge simultaneously on two adjacent slides.

For the sake of clarity, fluid and air supply tubing for the several slide treatment stations have been omitted from the drawings. It will be understood, however, that the fluid and air supply tubing are made long enough to permit the valve plate to rotate plus or minus approximately 190° from a home position at the rear of the apparatus so that each slide treatment station can reach each slide 1060.

With respect to FIGS. 11 and 14, reagent support 1300 is fixedly mounted to a cage 1110 vertically above nozzle support 1100, which cage in turn is rotatably mounted for rotation on a shaft 1113, which in turn is driven by a stepper motor and belt (not shown). A plurality of reagent dispensers 1302 are removably mounted equally spaced adjacent the periphery of reagent support 1300. In the illustrated embodiment, a total of thirty-five reagent dispensers are carried by the reagent support 1300, spaced approximately one thirty-fifth (approximately 10°) apart. Preferably, the reagent dispensers are mounted on curved dispenser carriers 1303, which in turn are mounted on reagent support 1300 (see FIG. 17A).

Curved dispenser carrier 1303 permits a lab worker to assemble a kit of reagent dispensers for use, and also to remove the kit of reagent dispensers so that the reagents may be refrigerated, for example, overnight when not in use.

The reagents may include any chemical or biological material conventionally applied to slides including nucleic acid probes or primers, polymerase, primary and secondary antibodies, digestion enzymes, pre-fixatives, post-fixatives, readout chemistry, counterstains, and the like.

Figure 17A:
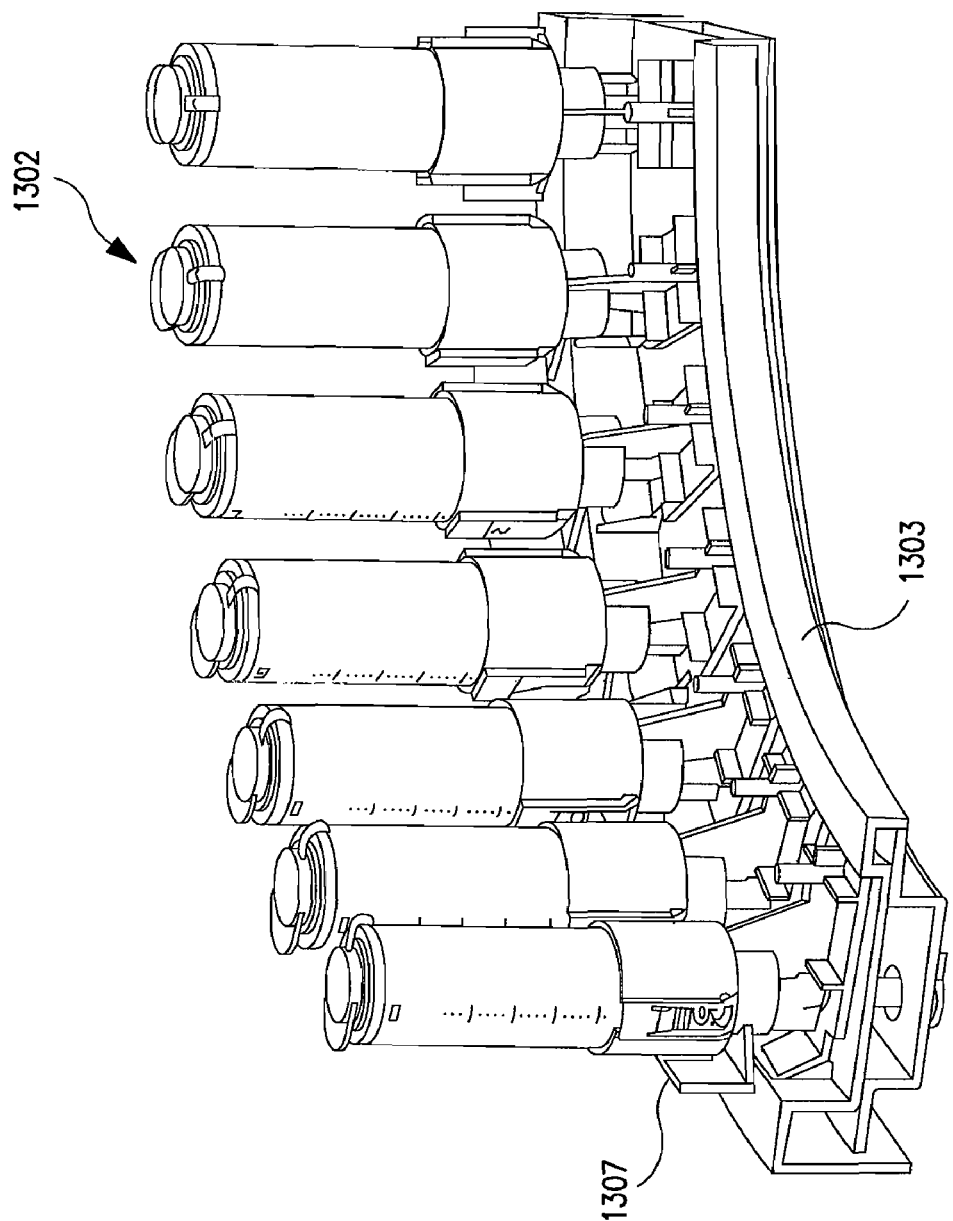
FIGS. 17A and 17B are front and rear perspective views of the reagent dispenser and dispenser carrier portion of the FIG. 11 alternative embodiment.
Figure 17B:
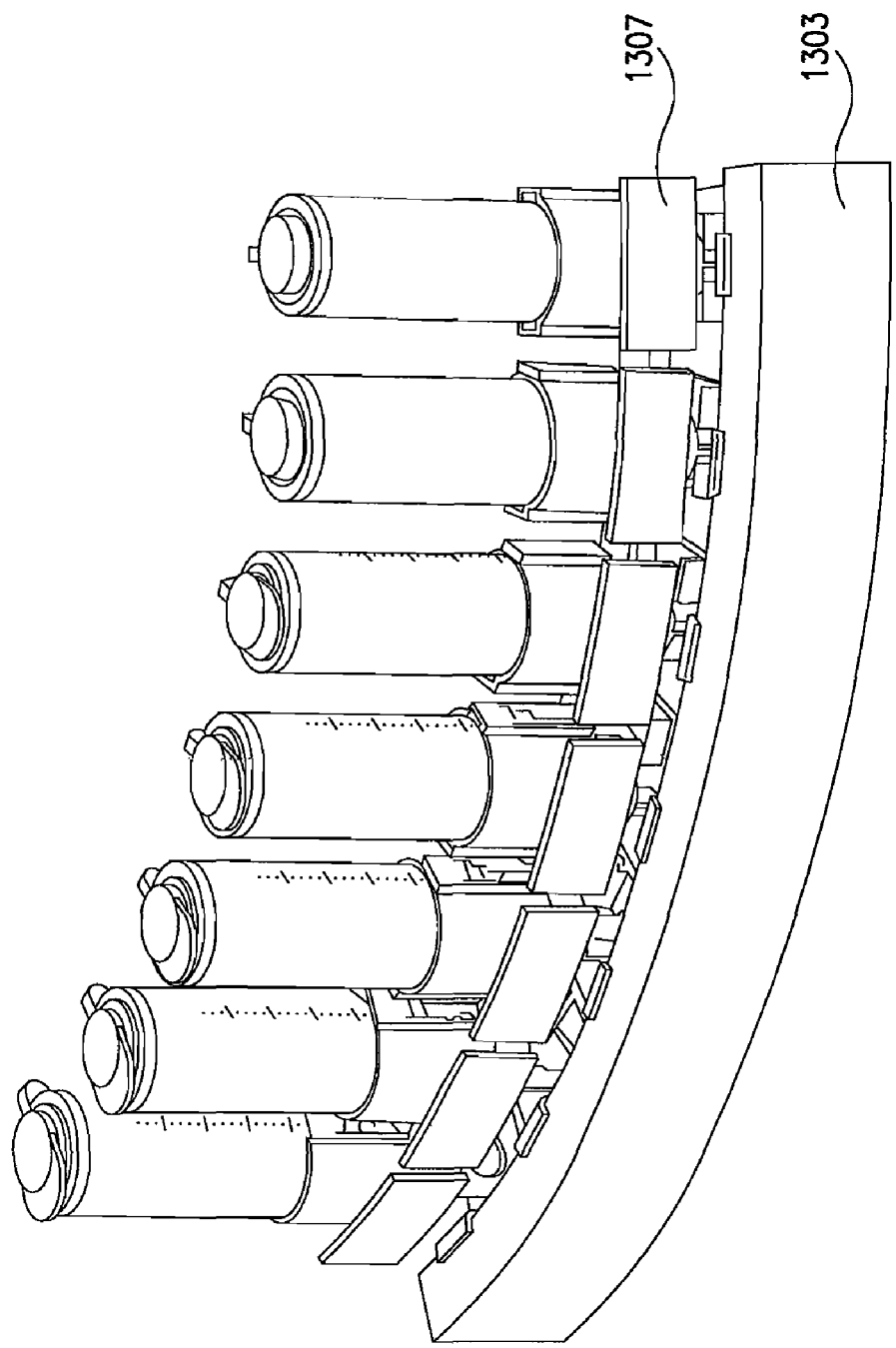

Referring in particular to FIGS. 17A and 17B, the reagent dispensers 1302, are shown mounted on dispenser carrier 1303.

Referring to both FIGS. 17A and 17B, each of the dispensers 1302 carries a plate 1307 upon which may be mounted a bar code which may be read by a bar code reader (not shown).

Referring also to FIG. 18, a hammer or piston 1400 is carried by an arm 1402 which is mounted on shaft 1113 for rotation with the shaft. Hammer 1400 is keyed to move with the nozzle support 1100, and is vertically and concentrically operatively aligned over the reagent dispensers 1302. Hammer or piston 1400 comprises a servo or piston 1404 for moving vertically into engagement with the top of a selected reagent dispenser, and force a metered quantity of reagent from the dispenser i.e. as explained in detail in U.S. Pat. No. 6,192,945. Thus, in order to dispense a selected reagent on a selected slide, the nozzle support 1100 is rotatably moved to a dispense position vertically over the selected slide which had been previously prepared, e.g. washed, etc., by the treatment stations carried on the nozzle support 1100. Since the hammer is keyed to move with the nozzle support 1100, there is no time wasted in moving the hammer or piston, and the hammer or piston is vertically aligned. A particular feature and advantage of the present invention is that the reagent support 1300 requires neither electrical nor plumbing connections. Thus, the reagent support 1300 is free to rotate in any direction, without limitation.

Figure 19A:
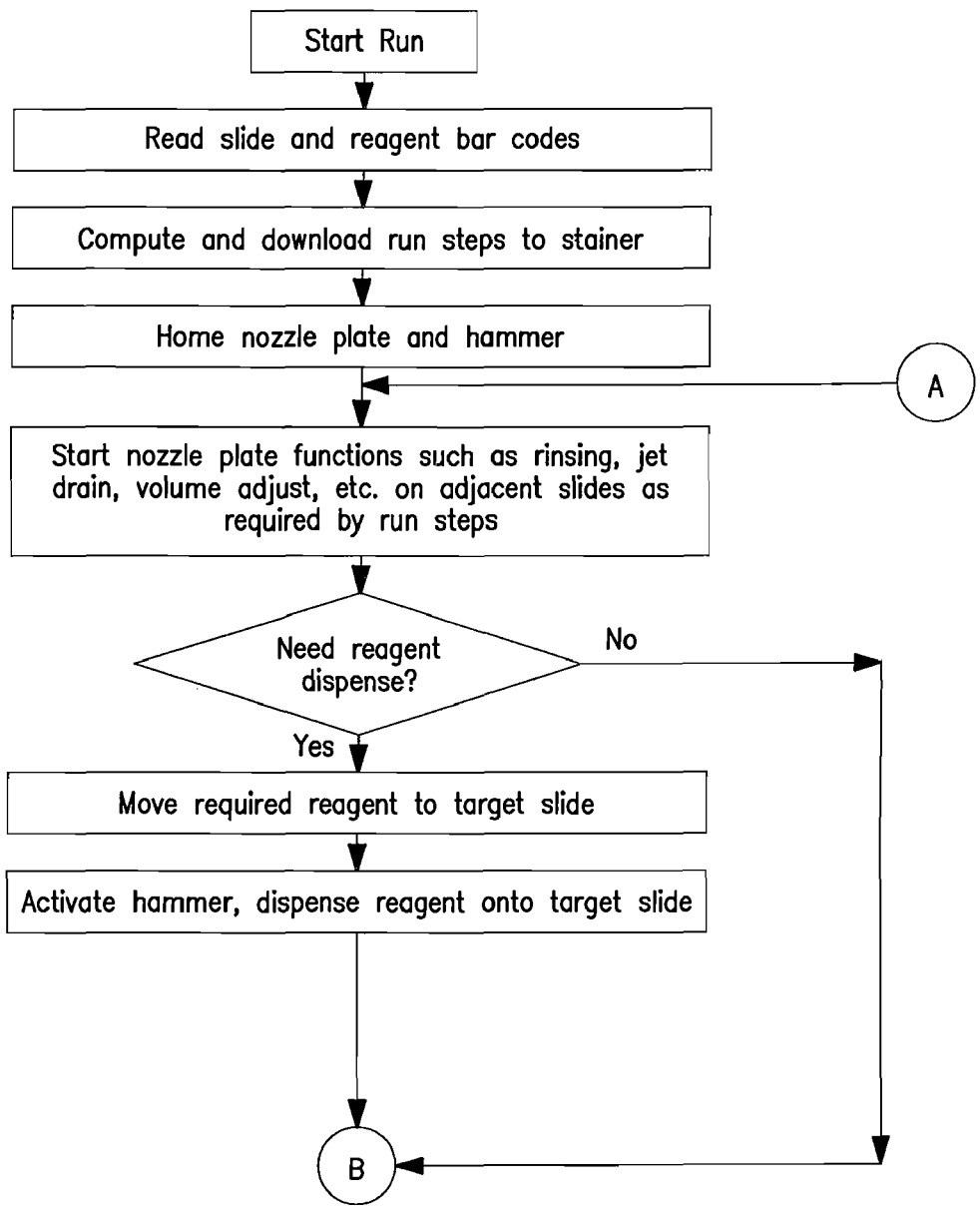
FIGS. 19A and 19B are flow charts of the operation and control of the FIG. 11 alternative embodiment.
Figure 19B:
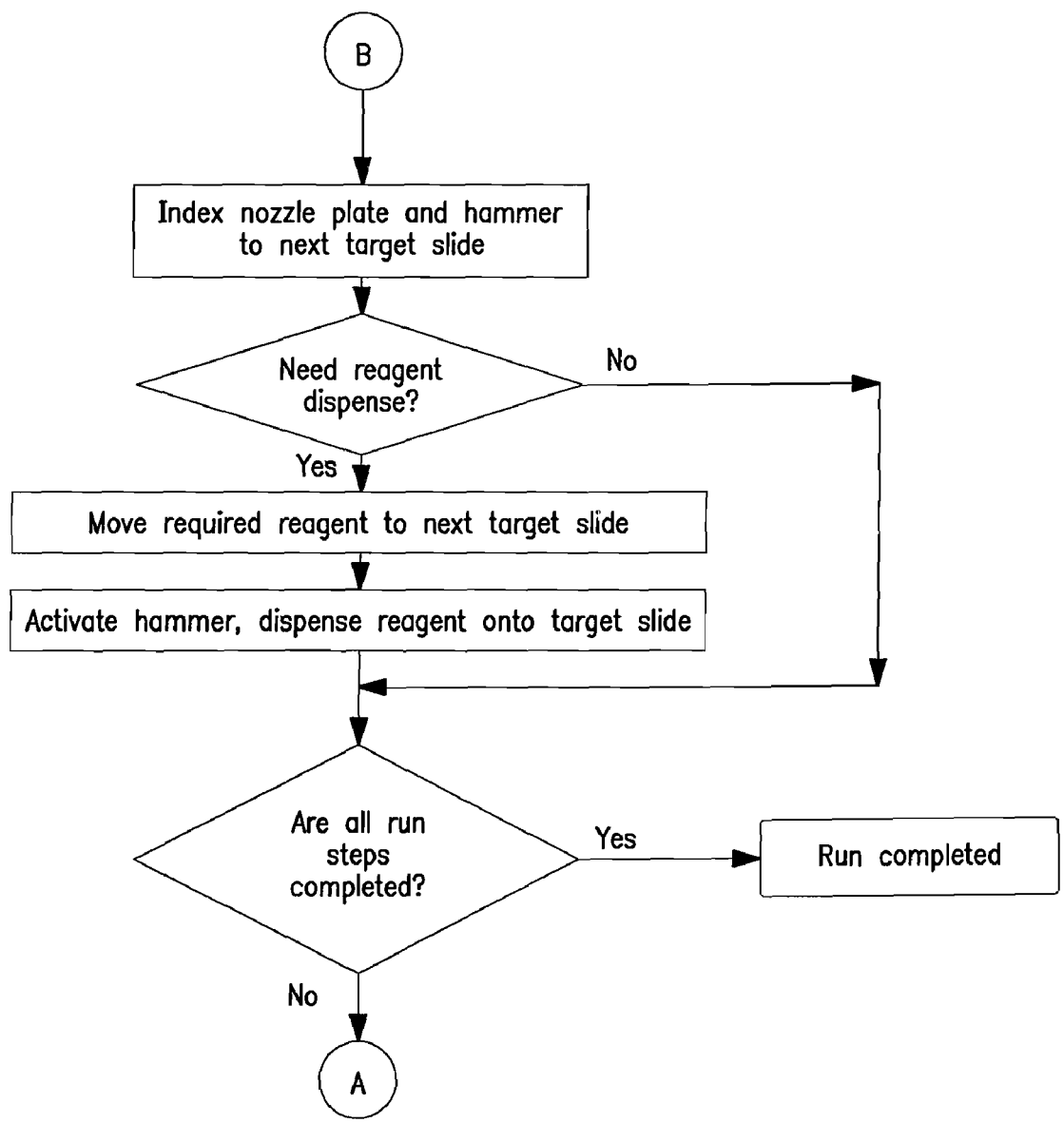

Referring to FIGS. 19A and 19B, the overall process is as follows:

A plurality of specimen-bearing slides 1060 are mounted on the slide platforms 1050, and selected reagent dispensers 1302 are mounted on the reagent support 1300. The slide drawer is closed and the slide and reagent bar codes are read. The computer calculates the master protocol and then downloads the run steps for the entire run, the nozzle support 1100 and hammer or piston 1400 are indexed to the first slide, and the slide is washed and prepared for staining or other treatment in accordance with the pre-programmed run steps by advancing the nozzle support 1100 in "lock-step" manner. In the meanwhile, reagent support 1300 is rotated to locate a selected reagent dispenser 1302 over the selected slide 1060, and the hammer or piston 1400 activated to dispense a measured amount of the desired reagent. The process is repeated for a second selected slide, and so forth.

Still other changes may be made without departing from the spirit and scope of the invention.

What is claimed is:

1. An automated method for processing at least one slide having a biological sample thereon comprising the steps of:
   providing a slide processing apparatus comprising:
   a computer;
   a rotatable reagent support;
   a rotatable nozzle support carrying at least one wash station;
   a movable slide drawer comprising a plurality of slide platforms radially and fixedly mounted thereon, and
   at least two movable reagent transfer probes carried above said plurality of slide platforms,
   wherein said slide platforms and said movable slide drawer are immovable while a master apparatus run protocol is in operation;
   opening said slide drawer;
   mounting one or more slides, each having a biological sample thereon, each on one of said plurality of said slide platforms;
   mounting at least two pre-selected reagent bottles on said reagent support;
   closing said slide drawer;
   automatedly determining the identity of said reagent bottles and slides mounted in said slide processing apparatus by automatedly reading identifying information carried on said reagent bottles and on slides carried on said slide platforms;
   automatedly computing and downloading a master apparatus run protocol based on the identity of said reagent bottles and slides mounted in said slide processing apparatus;
   automatedly moving said nozzle support relative to said plurality of slide platorms according to said master apparatus run protocol;
   automatedly moving said at least two transfer probes relative to said plurality of slide platforms according to said master apparatus run protocol;
   automatedly transferring predetermined volumes of reagents from said reagent bottles to slides carried on said plurality of slide platforms with at least one of said at least two transfer probes according to said master apparatus run protocol;
   automatedly washing at least one of said at least two transfer probes in said wash station; and
   automatedly heating said plurality of slides via said slide platform and according to said master apparatus run protocol,
   wherein the computer performs the automated steps and two of said automated steps can be performed simultaneously.

2. The automated method of claim 1, wherein the nozzle support and said reagent support are mounted concentrically above said slide drawer.

3. The automated method of claim 1, wherein said step of dispensing and said step of washing can be performed simultaneously.

* * * * *